(12) United States Patent
Xu et al.

(10) Patent No.: US 8,067,212 B2
(45) Date of Patent: Nov. 29, 2011

(54) BACILLUS PUMILUS STRAIN FOR HIGH YIELD OF TETRAMETHYLPYRAZINE

(75) Inventors: Ping Xu, Shanghai (CN); Zijun Xiao, Shanghai (CN); Zhonghao Wei, Shanghai (CN); Yi Du, Shanghai (CN)

(73) Assignee: Shanghai Apple Flavor & Fragrance Co., Ltd., Shanghai (CN)

( * ) Notice: Subject to any disclaimer, the term of this patent is extended or adjusted under 35 U.S.C. 154(b) by 304 days.

(21) Appl. No.: 12/302,275

(22) PCT Filed: May 25, 2007

(86) PCT No.: PCT/CN2007/001705
§ 371 (c)(1),
(2), (4) Date: Nov. 24, 2008

(87) PCT Pub. No.: WO2007/137510
PCT Pub. Date: Dec. 6, 2007

(65) Prior Publication Data
US 2009/0275108 A1    Nov. 5, 2009

(30) Foreign Application Priority Data

May 26, 2006    (CN) .......................... 2006 1 0026927

(51) Int. Cl.
*C12P 17/00* (2006.01)
*C12N 1/20* (2006.01)
(52) U.S. Cl. .................. 435/117; 435/252.5; 435/252.1; 435/832
(58) Field of Classification Search .......................... None
See application file for complete search history.

(56) References Cited

U.S. PATENT DOCUMENTS

| 4,701,413 | A | 10/1987 | Miyagawa et al. | ............. | 435/88 |
| 5,869,038 | A | 2/1999 | Leifert et al. | ................ | 424/93.4 |

FOREIGN PATENT DOCUMENTS

| FR | 2 728 913 | A1 | 7/1996 |
| KR | 1994-0005652 | | 6/1994 |

OTHER PUBLICATIONS

Ouoba et al. "Volatile compounds of Soumbala, a fermented African locust bean (*Parkia biglobosa*) food condiment". Journal of Applied Microbiology. 2005, 99, pp. 1413-1421.
Slepecky et al. In: "The Prokaryotes"; 1992, 2nd edition, vol. II, pp. 1663-1669 and p. 1762.
Demyttenaere et al., "Production of pyrazines and 2-acetyl-1-pyrroline by *Bacillus cereus* strains," *Flavour Research at the Dawn of the Twenty-First Century*, Abstract, pp. 344-349, Lavoisier, France (2003).
Larroche et al., "High pyrazine production by *Bacillus subtilis* in solid substrate fermentation on ground soybeans," *Process Biochemistry*, 34: 667-674 (1999).
Xiao et al., "Tetramethylpyrazine production from glucose by a newly isolated *Bacillus* mutant," *Appl. Microbiol. Biotechnol.*, 73: 512-518 (2006).
Ouoba, L., et al., "Genotyping of Starter Cultures of *Bacillus subtilis* and *Bacillus pumilus* for Fermentation of African Locust Bean (*Parkia biglobosa*) to Produce Soumbala," International Journal of Food Microbiology 90:197-205 (2004).

*Primary Examiner* — Vera Afremova
(74) *Attorney, Agent, or Firm* — Finnegan, Henderson, Farabow, Garrett & Dunner, LLP

(57) ABSTRACT

This invention provides a high-yield bacterial strain for producing tetramethylpyrazine named *Bacillus pumilus* RX3-17. The strain has been deposited in China Center for Type Culture Collection on Apr. 19, 2006. The deposit number is CCTCC M 206043. The bacterial strain, isolated from soil, is rod-shaped, 1.5 μm to 3.0 μm in length and 0.6 μm to 0.7 μm in diameter. The colony color of the strain is milky-white. The strain has typical physiological and biochemical characteristics of *Bacillus pumilus*. The 16s rDNA sequence of this strain shares a similarity of 99% with other *Bacillus pumilus* strains. This invention belongs to the domain of biotechnology. The strain can be applied to the production of tetramethylpyrazine with glucose as the substrate, solving the bottleneck of low yield in bacterial tetramethylpyrazine fermentation.

12 Claims, 1 Drawing Sheet

BACILLUS PUMILUS STRAIN FOR HIGH YIELD OF TETRAMETHYLPYRAZINE

This application claims priority to PCT International Application No. PCT/CN2007/001705 filed May 25, 2007, now International Publication No. WO 2007/137510, which claims the benefit of Chinese Patent Application No. 200610026927.8, filed May 26, 2006, all of which are incorporated herein by reference.

FIELD OF THE INVENTION

This invention belongs to the domain of biotechnology. Concretely speaking, this invention relates to a newly isolated high-yield tetramethylpyrazine-producing *Bacillus pumilus* strain.

BACKGROUND OF THE INVENTION

Tetramethylpyrazine was originally isolated from *Ligusticum wallichii* in 1957. Tetramethylpyrazine, whose tonality could be described as cocoa, coffee, lactose, vine, and galbanum, is wildly used as flavoring additive in food, tobacco, and alcohol industries. It is the main biologically active alkaloid existing in the Chinese herb Chuanxiong which improves blood circulation, tonifies qi and removes blood clots and is routinely used in China as medicaments for several diseases, such as heart-and-brain's vein disease, breath system disease and glomerular disease.

There are three methods, i.e. biosynthetic method, direct extraction from plants, and chemical synthetic method, for tetramethylpyrazine production.

As to biosynthesis of tetramethylpyrazine, the application of biotechnology mainly refers to microbial technology which includes screening and mutation of strains and fermentation technology. To date, there are some such reports out side of China and mainly in France, Japan, Germany, and the US.

Tetramethylpyrazine can be fermented from some kinds of sugars. The current research status of biosynthesis of tetramethylpyrazine is as follows.

Kosuge et al. firstly identified that some microbes are capable of pyrazine production and they found *Bacillus subtilis* was a tetramethylpyrazine producer in 1962. Now people know that some bacteria and epiphyte can synthesize different kinds of alkyl pyrazines (Seitz, 1994; Gallois, 1984). Yamaguchi et al. once tried to utilize these microorganisms in submerged fermentation but failed in industrialization because of the too low product concentration in fermentation broth (1993).

Itohiki-natto is one of the most popular fermentative foods due to its special pyrazine flavor. It is fermented from *Bacillus natto* on soybean solid medium by Japanese. However, the results were poor for solid-state fermentations were experiential methods. The yield of flavor substances was less than 22 µg/kg wet weight (Kosuge et al. 1971).

Besson et al. from France did a lot of work in this field. They yield 0.58 g/kg utilizing *Bacillus subtilis* IFO 3013 by solid-state fermentation on soybean medium (1998). This was the best result reported of tetramethylpyrazine biosynthetic methods. But there are still great efforts before the realization of industrialization.

Due to the low concentration of tetramethylpyrazine in plants, extraction of tetramethylpyrazine from plant materials is a costly technology and unfit for industrialization. While the method of chemical synthesis can bring in high yield of tetramethylpyrazine, it demands intensive reaction conditions and more sophisticated equipments. Moreover, the resulting tetramethylpyrazine is not regarded as natural product and there are serious problem in protecting environment. In contrast, the method of biosynthesis has the advantages such as natural product, low material costs, mild reaction conditions, environmentally benign and is considered as the future study of tetramethylpyrazine synthesis with very good prospects. However, isolation of tetramethylpyrazine producing strains from nature is a difficult job and yields from wild strains obtained by this way are usually low. As well as the low start base of other microbial ways, technologies of tetramethylpyrazine production by biosynthesis are immature and have not been industrialized.

SUMMARY OF THE INVENTION

Due to the current difficulties and problems with tetramethylpyrazine production, the aim of this invention is to supply a newly isolated high-yield *Bacillus pumilus* for producing tetramethylpyrazine with the substrate of glucose, which can be employed in tetramethylpyrazine fermentation.

The strain *Bacillus pumilus* RX3-17 in this invention has been deposited in China Center for Type Culture Collection on Apr. 19, 2006. The deposit number is CCTCC M 206043.

The physiological and biochemistry characteristics of *Bacillus pumilus* RX3-17 CCTCC M 206043 are described in Table 1.

Table 1 Physiological and biochemistry characteristics of the strain *Bacillus pumilus* RX3-17 CCTCC M 206043

| Characteristics | Results |
| --- | --- |
| Rods | + |
| Width | 0.6~0.7 µm |
| Length | 1.5~3.0 µm |
| Spores | + |
| Ellipsoid | + |
| Sporangium | − |
| VP reaction | + |
| pH in VP | 5.0 |
| Acid from glucose | + |
| Acid from arabinose | + |
| Acid from xylose | + |
| Acid from mannitol | + |
| Acid from fructose | + |
| Gas from glucose | − |
| Hydrolysis of casein | + |
| Hydrolysis of gelatin | + |
| Hydrolysis of starch | − |
| Hydrolysis of Tween 80 | + |
| Hydrolysis of esculine | − |
| Utilization of citrate | + |
| Utilization of propionate | − |
| Degradation of tyrosin | − |
| Phenylalanin deaminase | − |
| $NO_3$ to $NO_2$ | − |
| Indol | − |
| Growth at pH 5.7 | + |
| Growth with 2% NaCl | + |
| Growth with 5% NaCl | + |
| Growth with 7% NaCl | + |
| Growth with 10% NaCl | + |
| Growth at 45° C. | + |
| Growth at 50° C. | + |
| Growth at 55° C. | − |
| Growth with 0.001% lysozym | + |
| Arginin dihydrolase | − |

The 16S rDNA sequence of *Bacillus pumilus* RX3-17 CCTCC M 206043 is 99% similar to other *Bacillus pumilus* strains.

The above-mentioned strain *Bacillus pumilus* RX3-17 CCTCC M 206043 is employed in tetramethylpyrazine production with the SV fermentation medium which contains (per liter distilled water) 160~220 g glucose, 50 g soytone, 30 g $(NH_4)_2HPO_4$, and 15 ml vitamin mixture solution. The vitamin mixture solution contains (per liter distilled water) 1.0 mg d-biotin, 1.0 mg thiamine-HCl, 5.0 mg riboflavin, 25 mg pyridoxine-HCl, 50 mg p-aminobenzoic acid, 100 mg pantothenate-1/2 Ca, and 100 mg nicotinic acid.

When using the above-mentioned *Bacillus pumilus* RX3-17 CCTCC M 206043 to produce tetramethylpyrazine with the SV fermentation medium, the temperature of fermentation is 37° C. and the strain is inoculated in 50 ml of the SV fermentation medium in 500-ml conical flasks which are kept on a shaker at 120 r/min for 96~120 h to obtain the mature tetramethylpyrazine fermentation broth.

The present invention overcomes the bottleneck of tetramethylpyrazine fermentation, i.e. low concentration of the fermentation product, by providing the high-yield tetramethylpyrazine-producing strain *Bacillus pumilus* RX3-17 CCTCC M 206043. The approach of tetramethylpyrazine production by microbial fermentation has the advantages of low material costs, mild reaction conditions, natural product, low cost, and environmentally benign.

BRIEF DESCRIPTION OF THE DRAWINGS

The strain *Bacillus pumilus* RX3-17 in this invention has been deposited in China Center for Type Culture Collection on Apr. 19, 2006. The deposit number is CCTCC M 206043.

EXAMPLES

Example 1

Figure 1:
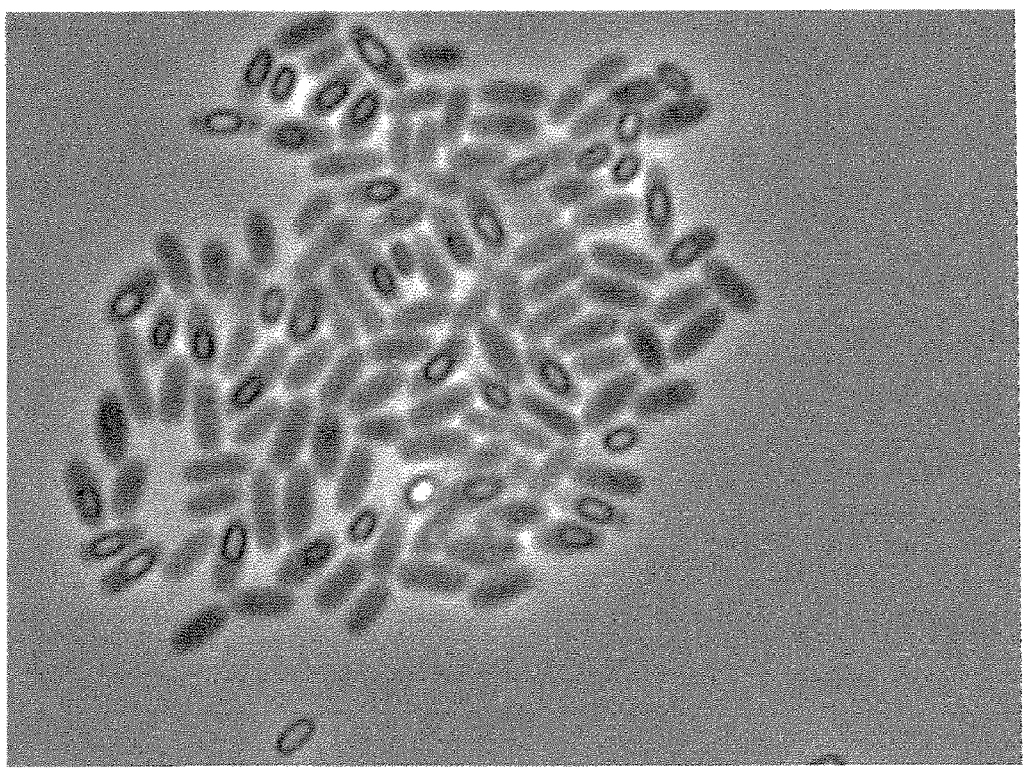
FIG. 1 shows the electron microscopy image (2700 fold) of the strain *Bacillus pumilus* RX3-17 CCTCC M 206043 in the present invention.

Step 1: Screening and Mutation to Obtain *Bacillus pumilus* RX3-17 CCTCC M 206043

Soil samples from apple orchards and vineyards were suspended in saline and heated at 80° C. for 10 min, then streaked onto nutrient agar and incubated at 37° C. for screening. The medium of the nutrient agar contains (per liter distilled water) 10 g peptone, 3 g beef extract, 5 g NaCl, and 18 g agar. The initial pH of the medium was 7.2. The medium was sterilized at 121° C. for 15 min.

Single colonies were isolated and inoculated in nutrient broth at 37° C. with shaking at 120 r/min. Cell suspensions at the mid-logarithmic stage were treated with 0.5 mg $l^{-1}$ nitrosoguanidine in 0.05 mol $l^{-1}$ Tris-maleic acid buffer (pH 6.0) for 30 min. The mutation procedure was terminated by diluting the reactant. After a 5-h incubation with shaking at 37° C., the culture was diluted properly and streaked onto nutrient agar for further isolation and screening. The preparation method of the nutrient broth medium was same as the nutrient agar medium, only excepting that agar was not added.

The strain, isolated by the above-mentioned methods, was identified by physiological and biochemistry experiments. It is rod in shape, 1.5 μm to 3.0 μm in length and 0.6 μm to 0.7 μm in diameter. The colony color of the bacterial strain is milky-white. It can produce spores and the VP reaction is positive. It can utilize glucose, arabinose, xylose, mannitol, or fructose to form acids. The bacterial strain can also hydrolyze casein, gelatin and Tween 80, utilize citrate, grow in medium containing 10% (w/w) NaCl, and grow at 50° C. The 16S rDNA sequence of this strain shares 99% similarity with other *Bacillus pumilus* strains.

The strain was named as *Bacillus pumilus* RX3-17 and it has been deposited in China Center for Type Culture Collection on Apr. 19, 2006 with the deposit number CCTCC M 206043.

Step 2: Preparation of Cell Broth of the Above-mentioned Strain *Bacillus pumilus* RX3-17 CCTCC M 206043

A loop of the strain *Bacillus pumilus* RX3-17 CCTCC M 206043 cultured on nutrient agar slant was inoculated in a 300-ml conical flask containing 25 ml sterilized nutrient broth and cultivated at 37° C. with shaking at 120 r/min for 12 h to get the resulting cell broth.

Step 3: Preparation of Mature Tetramethylpyrazine Fermentation Broth Using the Above-mentioned Strain *Bacillus pumilus* RX3-17 CCTCC M 206043 and the SV Fermentation Medium Containing 160 g/L Glucose The cell broth obtained from step 2 was inoculated at a volume ratio of 6% (v/v) to 500-ml conical flasks each of which contained 50 ml of sterilized SV fermentation medium. The bacterium was cultured at 37° C. with shaking at 120 r/min. When the concentration of tetramethylpyrazine reached 1.50±0.07 g/L at 96 h, the mature tetramethylpyrazine fermentation broth was obtained.

The components of the above-mentioned SV fermentation medium containing 160 g/L glucose were as follows. One liter of distilled water contained 160 g glucose, 50 g soytone, 30 g $(NH_4)_2HPO_4$, and 15 ml vitamin mixture solution. The pH was adjusted to 7.0. The vitamin mixture solution contained (per liter distilled water) 1.0 mg d-biotin, 1.0 mg thiamine-HCl, 5.0 mg riboflavin, 25 mg pyridoxine-HCl, 50 mg p-aminobenzoic acid, 100 mg pantothenate-1/2 Ca, and 100 mg nicotinic acid.

Example 2

Preparation of Mature Tetramethylpyrazine Fermentation Broth Using Strain *Bacillus pumilus* RX3-17 CCTCC M 206043 Obtained from Example 1 Step 1 and 2, and the SV Fermentation Medium Containing 180 g/L Glucose EXAMPLE 2 was performed with altered glucose concentration of 180 g/L according to EXAMPLE 1 step 3. When the concentration of tetramethylpyrazine reached 1.79±0.08 g/L at 104 h, the mature tetramethylpyrazine fermentation broth was obtained.

Example 3

Preparation of Mature Tetramethylpyrazine Fermentation Broth Using Strain *Bacillus pumilus* RX3-17 CCTCC M 206043 Obtained from Example 1 Step 1 and 2, and the SV Fermentation Medium Containing 200 g/L Glucose EXAMPLE 3 was performed with altered glucose concentration of 200 g/L according to EXAMPLE 1 step 3. When the concentration of tetramethylpyrazine reached 2.22±0.06 g/L at 112 h, the mature tetramethylpyrazine fermentation broth was obtained.

Example 4

Preparation of Mature Tetramethylpyrazine Fermentation Broth Using Strain *Bacillus pumilus* RX3-17 CCTCC M 206043 Obtained from Example 1 Step 1 and 2, and the SV Fermentation Medium Containing 220 g/L Glucose EXAMPLE 3 was performed with altered glucose concentration of 220 g/L according to EXAMPLE 1 step 3. When the concentration of tetramethylpyrazine reached 1.67±0.05 g/L at 120 h, the mature tetramethylpyrazine fermentation broth was obtained.

What is claimed is:

1. An isolated *Bacillus pumilus* strain that produces a high yield of tetramethylpyrazine wherein the *Bacillus pumilus* strain is characterized by the following properties: a rod-shaped bacterium with a length of 1.5 to 3.0 μm and a diameter of 0.6 to 0.7 μm; a colony color of milky-white; a capability of sporulation; a positive VP reaction; an ability to produce acid when cultured with glucose, arabinose, xylose, mannitol, or fructose; an ability to hydrolyze casein, gelatin, and Tween 80; an ability to produce a high yield of tetramethylpyrazine with glucose as a substrate in a fermentation medium; an inability to hydrolyze esculine; an ability to utilize citrate as the carbon source; an ability to live in 10% NaCl solution (w/w) and grow under 50° C.; and a 16s rDNA sequence that shares a similarity of 99% with other *Bacillus pumilus* strains wherein the isolated *Bacillus pumilus* strain is designated *Bacillus pumilus* RX3-17, which is deposited in China Center for Type Culture Collection with the deposit number CCTCC M 206043.

2. A method for producing tetramethylpyrazine, comprising:
   (a) providing the isolated *Bacillus pumilus* strain according to claim 1;
   (b) introducing the isolated *Bacillus pumilus* strain into a fermentation medium comprising glucose;
   (c) allowing fermentation to proceed; and
   (d) obtaining a mature tetramethylpyrazine fermentation broth.

3. The method according to claim 2 wherein the fermentation medium further comprises soytone.

4. The method according to claim 2 wherein the fermentation medium comprises (per liter distilled water) 160 to 220 g glucose.

5. The method according to claim 4 wherein the fermentation medium further comprises a vitamin mixture.

6. The method according to claim 2 wherein the fermentation is allowed to proceed at 37° C. for 96 to 120 hours to obtain the mature tetramethylpyrazine fermentation broth.

7. An isolated *Bacillus pumilus* strain, wherein the strain is designated *Bacillus pumilus* RX3-17, which is deposited in China Center for Type Culture Collection with the deposit number CCTCC M 206043.

8. A method for producing tetramethylpyrazine, comprising:
   (a) providing the isolated *Bacillus pumilus* strain according to claim 7;
   (b) introducing the isolated *Bacillus pumilus* strain into a fermentation medium comprising glucose;
   (c) allowing fermentation to proceed; and
   (d) obtaining a mature tetramethylpyrazine fermentation broth.

9. The method according to claim 8 wherein the fermentation medium further comprises soytone.

10. The method according to claim 8 wherein the fermentation medium comprises (per liter distilled water) 160 to 220 g glucose.

11. The method according to claim 10 wherein the fermentation medium further comprises a vitamin mixture.

12. The method according to claim 8 wherein the fermentation is allowed to proceed at 37° C. for 96 to 120 hours to obtain the mature tetramethylpyrazine fermentation broth.

* * * * *